US009113786B2

(12) United States Patent
Li

(10) Patent No.: US 9,113,786 B2
(45) Date of Patent: Aug. 25, 2015

(54) DEVICES, SYSTEMS AND METHODS FOR IDENTIFYING POTENTIALLY DANGEROUS ONCOMING CARS

(71) Applicant: Po Yiu Pauline Li, Kennedy Town (HK)

(72) Inventor: Po Yiu Pauline Li, Kennedy Town (HK)

( * ) Notice: Subject to any disclaimer, the term of this patent is extended or adjusted under 35 U.S.C. 154(b) by 484 days.

(21) Appl. No.: 13/660,918

(22) Filed: Oct. 25, 2012

(65) Prior Publication Data

US 2014/0118523 A1 May 1, 2014

(51) Int. Cl.
*A61B 5/00* (2006.01)
*A61B 5/18* (2006.01)
*A61B 3/113* (2006.01)
*G06K 9/00* (2006.01)
*G06K 9/32* (2006.01)
*A61B 5/0496* (2006.01)

(52) U.S. Cl.
CPC .............. *A61B 5/0077* (2013.01); *A61B 3/113* (2013.01); *A61B 5/18* (2013.01); *G06K 9/00791* (2013.01); *G06K 9/00845* (2013.01); *G06K 9/325* (2013.01); *A61B 5/0496* (2013.01); *A61B 5/7445* (2013.01); *G06K 2209/15* (2013.01)

(58) Field of Classification Search
CPC ........ A61B 5/18; A61B 3/113; A61B 5/0496; A61B 5/0077; A61B 5/7445; A61B 3/14; A61B 5/4863; G06K 9/00; G06K 9/325; G06K 2209/15; G06K 9/00791; G06K 9/00845; B06W 50/14; B60K 28/02
See application file for complete search history.

(56) References Cited

U.S. PATENT DOCUMENTS

| | | | | |
|---|---|---|---|---|
| 6,529,831 | B1 * | 3/2003 | Smith et al. | 701/301 |
| 6,583,730 | B2 * | 6/2003 | Lang et al. | 340/905 |
| 8,899,748 | B1 * | 12/2014 | Migdal | 351/206 |
| 2007/0132950 | A1 * | 6/2007 | Victor et al. | 351/200 |
| 2012/0029813 | A1 * | 2/2012 | Tajima et al. | 701/300 |
| 2012/0201041 | A1 * | 8/2012 | Gergets et al. | 362/493 |
| 2013/0084010 | A1 * | 4/2013 | Ross et al. | 382/182 |

* cited by examiner

*Primary Examiner* — Sath V Perungavoor
*Assistant Examiner* — Xiaolan Xu
(74) *Attorney, Agent, or Firm* — Matthew M. DiMaggio, Esq.

(57) ABSTRACT

A device, a system, and/or a method are provided for monitoring the eye behavior of drivers of oncoming cars. A camera mounted to a car mirror may monitor the eyes of oncoming drivers. An eye recognition analyzer may recognize nystagmus symptoms exhibited by the oncoming drivers. A machine may recognize the license plate information of the oncoming cars. The license plate numbers, as well as other identifying features of the oncoming cars, may be displayed on a head-up display of a car. A driver of the car may be otherwise notified by an alarm and/or warning about the possibility of a dangerous, oncoming car. An emitter located on the car may emit signals to other nearby networked cars in order to warn their drivers about the dangerous oncoming car. Information regarding the dangerous oncoming car may be displayed on the head-up displays of the other nearby networked cars.

18 Claims, 2 Drawing Sheets

DEVICES, SYSTEMS AND METHODS FOR IDENTIFYING POTENTIALLY DANGEROUS ONCOMING CARS

FIELD OF THE INVENTION

This invention relates generally to an imaging system for use in a vehicle for detecting the presence of nearby cars that present nystagmus related-behavior, and, more particularly, to an imaging system for use in a vehicle that analyzes human eyes of nearby drivers, and uses information gathered for vehicle safety purposes.

BACKGROUND OF THE INVENTION

Traffic-related fatalities are one of the leading causes of death in many countries throughout the world. Many traffic accidents are due to temporary physical incapacitation of the driver. Such physical incapacitation may be, for example, due to the influence of drugs and/or alcohol, the effects of under sleeping, and/or the use of hand-held devices. While harsher punishments may discourage some people from partaking in volatile driving practices, they may not serve as a sufficient deterrent for all people. Oftentimes it is the other driver, who was practicing safe driving, who is injured or killed in accidents due to drunk driving or the like. Thus, the law-abiding citizen may feel powerless against the risk of encountering a nearby driver whose capacity to drive is in some way hindered.

Thus, many systems and devices exist for increasing driver safety. The most obvious of these are airbags and seatbelts. However, recent innovations have been introduced which monitor and/or regulate an under-slept or incapacitated driver's behavior. One example of such innovations is an in-car breathalyzer device which prevents the car from starting unless and until the driver blows and registers legal blood-alcohol content into the device. However, many ways exist to bypass this requirement, such as having another person blow into the device. Moreover, such devices are mainly only imposed upon people with prior driving-while-intoxicated convictions.

Another recent innovation has been devices and systems which monitor a user's eye activity. Such devices warn a driver with a vibration of the seat or steering wheel if they detect the driver to be nodding off while at the wheel. While such innovations are welcome, they do not serve to protect a driver from other nearby cars. No devices or systems exist which warn other drivers and/or police about a possibly incapacitated nearby driver. Such an innovation would be extremely useful because it would be the first to protect a driver from other drivers, as opposed to protecting a driver from himself/herself.

In view of the foregoing, there is a need for a device, system and method for warning other drivers about a possible incapacitated state of a driver a vehicle.

SUMMARY OF THE INVENTION

According to embodiments of the invention, a device, a system, and a method are provided for monitoring the eye behavior of drivers of oncoming cars. A camera mounted to a car mirror may monitor the eyes of oncoming drivers. An eye recognition analyzer may recognize nystagmus symptoms exhibited by the oncoming drivers. A machine may recognize the license plate information of the oncoming cars. The license plate numbers, as well as other identifying features of the oncoming cars, may be displayed on a head-up display of a car. A driver of the car may be otherwise notified by an alarm and/or warning about the possibility of a dangerous, oncoming car. An emitter located on the car may emit signals to other nearby networked cars in order to warn their drivers about the dangerous oncoming car. Information regarding the dangerous oncoming car may be displayed on the head-up displays of the other nearby networked cars.

In an embodiment of the disclosed invention, a car mirror which monitors nystagmus related-behavior to avoid a head-on collision is provided. The system's components may include: a car mirror, a camera placed on the car mirror, an eye recognition analyzer, a machine for recognizing license plate numbers, and a head-up display. The car mirror and associated camera may be placed on a driver side of a first car operated by a first driver. The camera is operable to film the eyes of an oncoming, second driver of a second car.

The eye recognition analyzer recognizes nystagmus symptoms of the second car driver. The eye recognition analyzer detects if any involuntary rhythmic shaking or wobbling of the eyes is found to exceed a pre-determined threshold value. The recognition may be carried out via software. The machine may recognize license plate numbers of the oncoming cars if those cars are determined to be dangerous. That is, the license plate numbers will be gathered only on cars whose drivers exhibit nystagmus symptoms. The head-up display warns the first driver about the possible dangerous propensity of the oncoming car.

The eye recognition analyzer may analyze both video and still images taken from the camera. The video and/or images may be analyzed for a specific eye movement which exceeds the pre-determined threshold criteria. The first driver may be notified of the second car by way of the license number of the second car, or by way of visual identification of the second car on the head-up display. If the second car is not in the periphery of the head-up display, the location of the second car may be identified to the driver.

In further embodiments of the car mirror, an emitter may be provided for sending warning signals to alert other nearby networked cars about the potentially dangerous oncoming car. The warning signals may have the license plate number of the second car be displayed on the head-up displays of the other nearby networked cars. In still further embodiments of the car mirror, an alarm device may be provided for alarming/notifying the first driver if/when an oncoming car crosses the center-line on the road.

In another embodiment of the disclosed invention, a method of identifying oncoming dangerous cars is provided. The method employs the following steps. The first step is directed providing a camera mounted to a first car driven by a first driver. The second step involves filming, with the camera, video of eyes of a second driver of an oncoming second car. The third step is directed to analyzing, using software, the video to determine if the eyes of the second driver exhibit nystagmus symptoms. Then, the first driver is notified if the second driver is determined to exhibit nystagmus symptoms. The step of notifying the first driver may be carried out via a head-up display on the windshield of the first car. The second car may be visually identified on the head-up display. Alternatively, the location of the second car may be identified on a display in the first car, such as, for example, an LCD screen.

In further embodiments of this method, an additional step may be provided of recognizing, with the camera, a license plate number of the second car. This step may further involve transmitting the license plate number to other nearby networked cars. In still a further embodiment, the software may analyze the video by detecting whether the eyes of the second driver exhibit involuntary rhythmic shaking or wobbling exceeding a pre-determined threshold value.

In yet another embodiment of the disclosed invention, a system for monitoring eye behavior of oncoming drivers is provided. The system may have a camera mounted on a car mirror placed on a driver side of a first car operated by a first driver. The camera is operable is film video of a second car driver of a second car coming in an opposite direction on a road. The system may also have an eye recognition analyzer for recognizing nystagmus symptoms of the second car driver. The eye recognition analyzer may operate by comparing images from the video to detect if any involuntary rhythmic shaking or wobbling of the eyes is found to exceed a pre-determined threshold value.

The system may have a machine that recognizes a license plate number of the second car using the camera when nystagmus symptoms are found by the analyzer. A head-up display may be provided in the first car for warning the first driver about the second car. The system may also have a receiver placed in the first car for receiving information from other networked cars about other dangerous cars. An emitter may send warning signals to alert the other networked cars. The warning signals may include the license plate number of the second car being displayed on head-up displays of the other networked cars. Finally, in the event that the second car has crossed the center-line, an alarm device is provided for alarming the first driver to be on alert.

It is, therefore, an objective of the disclosed invention to provide a device, a system and/or a method for identifying potentially hazardous cars by monitoring eye-activity of oncoming drivers.

In accordance with these and other objects which will become apparent hereinafter, the invention will now be described with particular reference to the drawings.

DETAILED DESCRIPTION

Referring now to the figures, a device, a system, and a method are provided for monitoring the eye behavior of drivers of oncoming cars. A camera mounted to a car mirror may monitor the eyes of oncoming drivers. An eye recognition analyzer may recognize nystagmus symptoms exhibited by the oncoming drivers. A machine may recognize the license plate information of the oncoming cars. The license plate numbers, as well as other identifying features of the oncoming cars, may be displayed on a head-up display of a car. A driver of the car may be otherwise notified by an alarm and/or warning about the possibility of a dangerous, oncoming car. An emitter located on the car may emit signals to other nearby networked cars in order to warn their drivers about the dangerous oncoming car. Information regarding the dangerous oncoming car may be displayed on the head-up displays of the other nearby networked cars.

Figure 1:
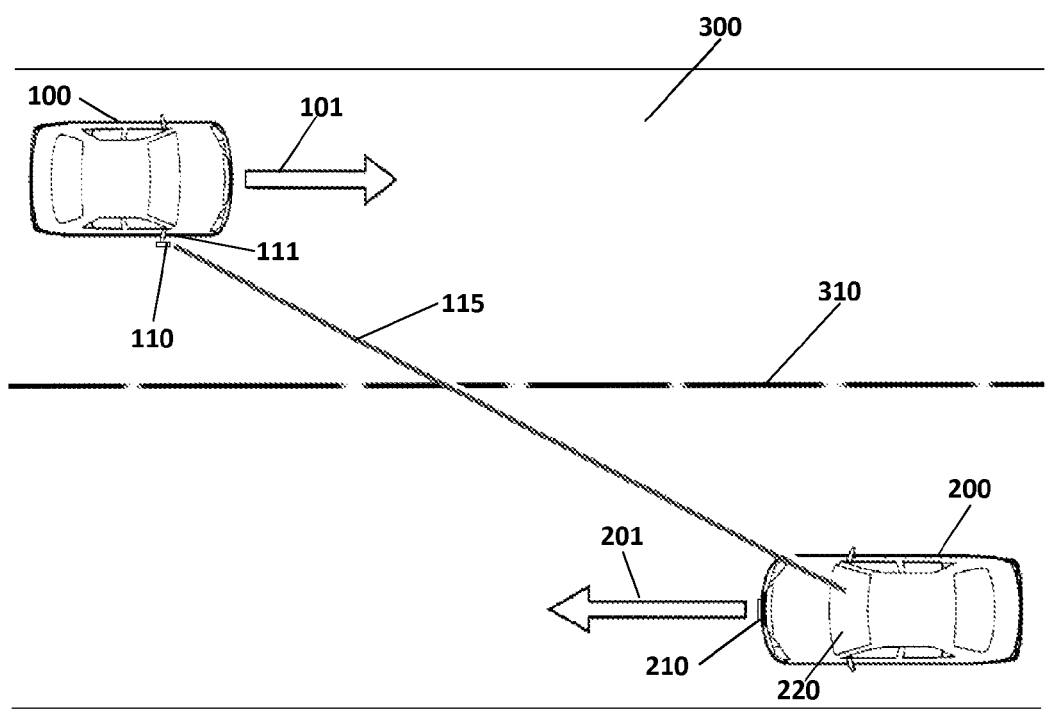
FIG. 1 is an overhead diagram of the monitoring system for drivers of oncoming cars according to an embodiment of the present invention.

Referring now to FIG. 1, an overhead diagram is shown of a monitoring system for drivers of oncoming cars according to an embodiment of the present invention. A first car 100 is shown driving in a first direction 101 along a road 300. A second car 200 (hereinafter referred to as "the second car" or "the oncoming car") is shown driving on the road 300 in a second direction 201, the second direction 201 being opposite to the first direction 101. A center-line 310 divides the road 300. A camera 110 is mounted to a driver side car mirror 111 of the first car 100. The camera 110 has a line-of-sight 115 which projects onto cars traveling in the opposite direction on the road 300. In FIG. 1, the line-of-sight 115 of the camera 110 is projected into a windshield 220 onto a driver (not shown) of the second car 200. Additionally, the camera 110 may be projected onto a license plate 210 of the second car 200.

The camera 110 may monitor the eyes of oncoming drivers. An eye recognition analyzer (not shown) may recognize nystagmus symptoms exhibited by the oncoming drivers. The eye recognition analyzer may be stored in the form of software, and may operate via processor. A machine (not shown) may read information on the license plate 210 of the second car 200.

Figure 2:
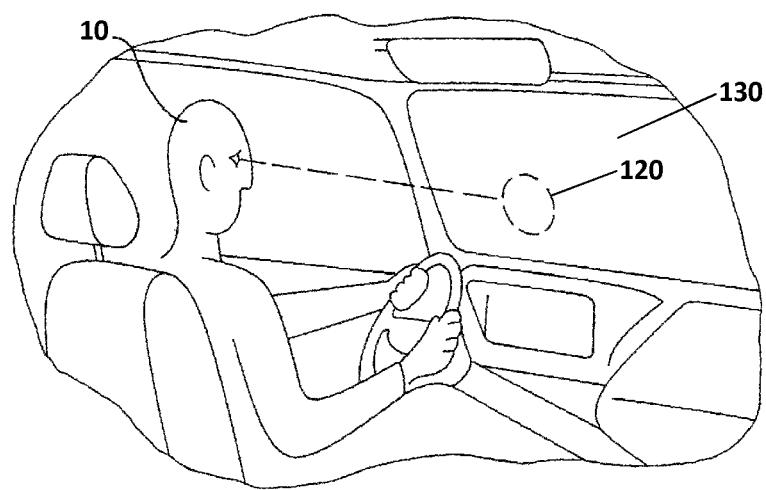
FIG. 2 is a perspective in-car view of a head-up display according to an embodiment of the present invention.

Referring now to FIG. 2, an interior of the first car 100 is shown. The first car 100 is driven by a first driver 10. The first car 100 may further have a head-up display ("HUD") 120. The license plate numbers, as well as other identifying features of the oncoming second car 200, may be displayed on a head-up display 120 of the first car 100. The driver 10 of the car 100 may be otherwise notified by an alarm and/or warning about the possibility of the dangerous, oncoming car 200. An emitter (not shown) located on the car may emit signals to other nearby networked cars in order to warn their drivers about the dangerous oncoming car 200 as well. Information regarding the dangerous oncoming car 200 may be displayed on the head-up displays of the other nearby networked cars. The information displayed may include the number of the license plate 210 of the second car 200.

In an embodiment of the disclosed invention, the car mirror 111 and associated camera 110 which monitors nystagmus related-behavior to avoid a head-on collision is provided. The system's components may include: the car mirror 111, a camera 110 placed on the car mirror 111, an eye recognition analyzer, a machine for recognizing license plate numbers, and a head-up display 120. The car mirror 111 and associated camera 110 may be placed on a driver side of a first car 100 operated by a first driver 10. The camera is operable to film the eyes of the second driver of the second car 200.

The eye recognition analyzer may recognize nystagmus symptoms of the second car driver. Nystagmus is a condition of voluntary or involuntary eye movement. Nystagmus may be caused by drugs, alcohol, central nervous system disorders, drowsiness, vertigo and/or numerous other incapacitating conditions. Symptoms of nystagmus may be exhibited by twitching, shaking, wobbling, or rhythmic moving of the eyes. When symptoms of nystagmus are present in a person, it may signify the presence of a physical condition which could severely inhibit that person's ability to handle simple tasks, such as driving. Thus, the appearance of nystagmus symptoms in a driver could be an indication that the driver's capacity to operate the car may be diminished. The ability to recognize nystagmus symptoms in other drivers should put a driver on alert to the possibility of the dangerous propensities of those other drivers.

The eye recognition analyzer detects if any involuntary rhythmic shaking or wobbling of the eyes is found to exceed a pre-determined threshold value. The recognition may be carried out via software. The analyzer may determine, for example, if a driver blinks or twitches his or her eye a certain number of times over a certain time interval. The machine may recognize license plate numbers of the oncoming cars if those cars are determined to be dangerous. That is, the license plate numbers will be gathered only on cars whose drivers exhibit nystagmus symptoms. The reading of license plate numbers may also be carried out by the camera 110. The head-up display 120 may warn the first driver 10 about the possible dangerous propensity of the oncoming car 200.

The eye recognition analyzer may analyze both video and still images taken from the camera 110. The video and/or images may be analyzed for a specific eye movement which exceeds the pre-determined threshold criteria. The first driver 10 may be notified of the dangerous propensity of the second car 200 by way of the license number 210 of the second car 200 or by way of visual identification of the second car 200 on the head-up display 120. If the second car 200 is in the periphery of the head-up display 120, the second car 200 may be highlighted or otherwise identified such that the physical proximity and/or location of the second car 200 is made apparent via the head-up display 120. If the second car 200 is not in the periphery of the head-up display 120, the location of the second car 200 may be identified to the driver 10. For example, if the second car 200 is behind an obstruction, the head-up display 120 may alert the driver 10 as to the approximate direction of the second car 200.

In further embodiments of the car mirror 111, an emitter may be provided for sending warning signals to alert other nearby networked cars about the potentially dangerous oncoming car 200. The warning signals may have the license plate number of the second car 200 be displayed on the head-up displays of the other nearby networked cars. In still further embodiments of the car mirror 111, an alarm device may be provided for alarming/notifying the first driver 10 if/when an oncoming car crosses the center-line 310 on the road 300.

In another embodiment of the disclosed invention, a method of identifying oncoming dangerous cars is provided. The method employs the following steps. The first step is directed providing a camera 110 mounted to a first car 100 driven by a first driver 10. The second step involves filming, with the camera 110, video of eyes of a second driver of an oncoming second car 200. The third step is directed to analyzing, using software, the video to determine if the eyes of the second driver exhibit nystagmus symptoms. Then, the first driver 10 is notified if the second driver is determined to exhibit nystagmus symptoms. The step of notifying the first driver 10 may be carried out via a head-up display 120 on the windshield 130 of the first car. The second car 200 may be visually identified on the head-up display 120. Alternatively, the location of the second car 200 may be identified on a display (not shown) in the first car 100, such as, for example, an LCD screen.

In further embodiments of this method, an additional step may be provided of recognizing, with the camera 110, a license plate number of a license plate 210 of the second car 200. This step may further involve transmitting the license plate number to other nearby networked cars. In still a further embodiment, the software may analyze the video by detecting whether the eyes of the second driver exhibit involuntary rhythmic shaking or wobbling exceeding a pre-determined threshold value.

In yet another embodiment of the disclosed invention, a system for monitoring eye behavior of oncoming drivers is provided. The system may have a camera 110 mounted on a car mirror 111 placed on a driver side of a first car 100 operated by a first driver 10. The camera 110 is operable is film video of a second car driver of a second car 200 traveling in an opposite direction 201 on a road 300. The system may also have an eye recognition analyzer for recognizing nystagmus symptoms of the second car driver. The eye recognition analyzer may operate by comparing images from the video to detect if any involuntary rhythmic shaking or wobbling of the eyes is found to exceed a pre-determined threshold value.

The system may have a machine that recognizes a license plate number of the second car 200 using the camera 110 when nystagmus symptoms are found by the analyzer. A head-up display 120 may be provided in the first car 100 for warning the first driver 10 about the second car 200. The system may also have a receiver placed in the first car 100 for receiving information from other networked cars about other dangerous cars. An emitter may send warning signals to alert the other networked cars. The warning signals may include the license plate number of the second car 200 being displayed on head-up displays 120 of the other networked cars. Finally, in the event that the second car 200 has crossed the center-line 310, an alarm device is provided for alarming the first driver 10 to be on alert.

While the disclosed invention has been taught with specific reference to the above embodiments, a person having ordinary skill in the art will recognize that changes can be made in form and detail without departing from the spirit and the scope of the invention. The described embodiments are to be considered in all respects only as illustrative and not restrictive. All changes that come within the meaning and range of equivalency of the claims are to be embraced within their scope. Combinations of any of the methods, systems, and devices described hereinabove are also contemplated and within the scope of the invention.

What is claimed is:

1. A car mirror which monitors nystagmus related-behavior to avoid a head-on collision, the car mirror comprising:
    a car mirror placed on a driver side of a first car operated by a first driver;
    a camera placed on the car mirror on the driver side of the first car wherein the camera films eyes of a second car driver of a second car coming in an opposite direction on a road;
    an eye recognition analyzer for recognizing nystagmus symptoms of the second car driver wherein the eye recognition analyzer detects if any involuntary rhythmic shaking or wobbling of the eyes is found to exceed a pre-determined threshold value;
    a machine for recognizing a license plate number of the second car using the camera when nystagmus symptoms are found by the analyzer; and
    a head-up display in the first car for warning the first driver about the second car.

2. The car mirror of claim 1, wherein the camera films video of the second driver and the eye recognition analyzer analyzes still images from the video.

3. The car mirror of claim 1 wherein the detection is limited to movement of eyes and excludes movement of a head of the second driver.

4. The car mirror of claim 1 wherein the warning comprises notifying the first driver that second driver has exhibited nystagmus symptoms.

5. The car mirror of claim 1 wherein the warning comprises the license plate number of the second car.

6. The car mirror of claim 1 further comprising an emitter that sends warning signals to alert other nearby networked cars wherein the warning signals comprise the license plate number of the second car being displayed on head-up displays of the other nearby networked cars.

7. The car mirror of claim 1 further comprising a receiver placed in the first car for receiving license plate numbers of other cars whose drivers have exhibited nystagmus symptoms wherein the license plate numbers are displayed on the head-up display.

8. The car mirror of claim 1, wherein the head-up display identifies the second car by a visual indication in a periphery of the head-up display.

9. The car mirror of claim 1, wherein the head-up display identifies a location of the second car if the second car is not in a periphery of the head-up display.

10. The car mirror of claim 1 further comprising an alarm device that alarms the first driver if the second car has crossed a center-line in the road.

11. A method of identifying oncoming dangerous cars comprising:
provurg a camera mounted to a first car driven by a first driver;
filming, with the camera, video of eyes of a second driver of an oncoming second car;
analyzing, using software, the video to determine if the eyes of the second driver exhibit nystagmus symptoms; and
notifying the first driver if the second driver is determined to exhibit nystagmus symptoms.

12. The method of claim 11, wherein the software analyzes the video by detecting whether the eyes of the second driver exhibit involuntary rhythmic shaking or wobbling exceeding a pre-determined threshold value.

13. The method of claim 11, wherein the step of notifying the first driver is carried out via a head-up display on a windshield of the first car.

14. The method of claim 11, wherein the step of notifying the first driver comprises visually identifying the second car on a head-up display on a windshield of the first car.

15. The method of claim 11, wherein the step of notifying the first driver comprises identifying the second car on a display of the first car.

16. The method of claim 11 further comprising:
recognizing, with the camera, a license plate number of the second car.

17. The method of claim 11 further comprising:
recognizing, with the camera, a license plate number of the second car; and
transmitting the license plate number to other nearby networked cars.

18. A system for monitoring eye behavior of oncoming drivers, the system comprising:
a car mirror placed on a driver side of a first car operated by a first driver;
a camera placed on the car mirror on the driver side of the first car wherein the camera films video of a second car driver of a second car coming in an opposite direction on a road;
an eye recognition analyzer for recognizing nystagmus symptoms of the second car driver wherein the eye recognition analyzer compares images from the video to detect if any involuntary rhythmic shaking or wobbling of the eyes is found to exceed a pre-determined threshold value;
a machine that recognizes a license plate number of the second car using the camera when nystagmus symptoms are found by the eye recognition analyzer; and
a head-up display in the first car for warning the first driver about the second car,
a receiver placed in the first car for receiving information from other networked cars about other dangerous cars;
an emitter that sends warning signals to alert the other networked cars wherein the warning signals comprise the license plate number of the second car being displayed on head-up displays of the other networked cars; and
an alarm device that alarms the first driver if the second car has crossed a center-line in the road.

* * * * *